United States Patent
Yamamichi et al.

(10) Patent No.: US 8,023,114 B2
(45) Date of Patent: Sep. 20, 2011

(54) TARGET SUBSTANCE DETECTING DEVICE, TARGET SUBSTANCE DETECTING METHOD USING THE SAME, AND DETECTING APPARATUS AND KIT THEREFOR

(75) Inventors: Junta Yamamichi, Yokohama (JP); Hidenori Shiotsuka, Kawasaki (JP); Tomohiro Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 53 days.

(21) Appl. No.: 11/914,500

(22) PCT Filed: Jul. 28, 2006

(86) PCT No.: PCT/JP2006/315448
§ 371 (c)(1),
(2), (4) Date: Apr. 1, 2008

(87) PCT Pub. No.: WO2007/015556
PCT Pub. Date: Feb. 8, 2007

(65) Prior Publication Data
US 2009/0128822 A1   May 21, 2009

(30) Foreign Application Priority Data
Aug. 1, 2005   (JP) ................................. 2005-223505

(51) Int. Cl.
*G01N 21/55* (2006.01)
(52) U.S. Cl. ........................................ 356/445; 435/7.1
(58) Field of Classification Search .................... 356/445
See application file for complete search history.

(56) References Cited

U.S. PATENT DOCUMENTS

| | | | |
|---|---|---|---|
| 6,331,276 B1 | 12/2001 | Takei et al. | |
| 6,579,721 B1 | 6/2003 | Natan et al. | |
| 6,768,556 B1 * | 7/2004 | Matsumoto et al. | 356/445 |
| 6,867,865 B2 | 3/2005 | Vaupel | |
| 7,307,731 B2 | 12/2007 | Naya | |
| 2003/0107741 A1 | 6/2003 | Pyo et al. | |
| 2003/0132392 A1 | 7/2003 | Kuroda et al. | |
| 2003/0164947 A1 * | 9/2003 | Vaupel | 356/445 |
| 2004/0183176 A1 | 9/2004 | Naya et al. | |
| 2004/0218185 A1 | 11/2004 | Yamada et al. | |

(Continued)

FOREIGN PATENT DOCUMENTS
EP    0 965 835 A2   12/1999
(Continued)

OTHER PUBLICATIONS

Zia et al. "Geometries and materials for subwavelength surface plasmon modes", J. Opt. Soc. Am. A, vol. 21, No. 12, Dec. 2004, pp. 2442-2446.*

(Continued)

*Primary Examiner* — Gregory J Toatley
*Assistant Examiner* — Rebecca C Slomski
(74) *Attorney, Agent, or Firm* — Fitzpatrick, Cella, Harper & Scinto

(57) ABSTRACT

A target substance detecting device, which is a device that has a substrate, a structure disposed on a substrate surface in isolation using a metal, and a target substance trapping substance disposed on the structure, and which is for detecting a target substance using localized plasmon resonance, characterized in that the above-mentioned structure is constructed by stacking at least two metal layers, sandwiching a non-conductive layer between the metal layers.

16 Claims, 10 Drawing Sheets

U.S. PATENT DOCUMENTS

| | | | |
|---|---|---|---|
| 2004/0263853 A1* | 12/2004 | Hill et al. ................ 356/445 |
| 2005/0045977 A1 | 3/2005 | Lin et al. |
| 2005/0287577 A1 | 12/2005 | Yamamichi |
| 2006/0108219 A1 | 5/2006 | Kuroda et al. |
| 2007/0090411 A1 | 4/2007 | Naya et al. |
| 2007/0127037 A1 | 6/2007 | Yamada et al. |
| 2007/0178522 A1 | 8/2007 | Shiotsuka et al. |
| 2008/0246970 A1* | 10/2008 | Kuroda et al. ............ 356/445 |

FOREIGN PATENT DOCUMENTS

| | | |
|---|---|---|
| EP | 1 445 601 A2 | 8/2004 |
| JP | 10-267841 A | 10/1998 |
| JP | 3452837 B2 | 7/2003 |
| JP | 2003-307488 A | 10/2003 |
| JP | 2004-239715 A | 8/2004 |
| JP | 2005-195440 A | 7/2005 |
| JP | 2005-312446 A | 11/2005 |
| JP | 2007-525466 A | 9/2007 |
| WO | 2004/068141 A1 | 8/2004 |
| WO | 2005/000900 A1 | 1/2005 |

OTHER PUBLICATIONS

Felicia Tam et al., "Geometrical Parameters Controlling Sensitivity of Nanoshell Plasmon Resonances to Changes in Dielectric Environment," 108(45) J. Phys. Chem. B. 17290-94 (2004).

Shigeru Toyama et al., "Design and Fabrication of a Waveguide-Coupled Prism Device for Surface Plasmon Resonance Sensor," Sensors and Actuators B; 65:32-34 (2000).

Official Action dated Sep. 3, 2009 in Canadian Application No. 2,609,023.

Official Action dated Dec. 20, 2010 in Canadian Application No. 2,609,023.

* cited by examiner

TARGET SUBSTANCE DETECTING DEVICE, TARGET SUBSTANCE DETECTING METHOD USING THE SAME, AND DETECTING APPARATUS AND KIT THEREFOR

TECHNICAL FIELD

The present invention relates to a target substance detecting device, a target substance detecting apparatus, a detecting method, and a detection kit, which are useful for detecting the presence of a target substance, such as a biological material, in a specimen.

BACKGROUND ART

In recent years, research related to surface plasmon resonance sensor using resonance excitation of a surface plasmon wave, which exists on a surface of a metal, by light has been advanced as one of the high sensitivity sensing systems. The wave number of the surface plasmon wave on a surface of the metal is determined by a dielectric constant of a medium that contacts the surface of the metal.

In a surface plasmon resonance sensor using surface plasmon resonance (SPR) in a metal thin film covering one aspect of a prism, since a surface plasmon wave cannot be excited by light that propagates through the air, evanescent light, which is generated at the time of total reflection and which is non-propagating light, is used. Therefore, such a sensor needs a total reflection optical system for generating the evanescent light. A surface plasmon resonance sensor, which excites a surface plasmon wave by stacking a metal thin film, a dielectric thin film, and a metal thin film in this order on a prism, and making light from a light source totally reflect on the metal thin film, is disclosed in Japanese Patent Application Laid-Open No. H10-267841.

A localized plasmon is excited by making light, spreading the air, enter nanometer size of metal structure. Hence, a sensor using the localized plasmon does not need a total reflection optical system, but is applicable to various forms of sensors. There is a known measuring method in which metal fine particles are fixed on a substrate surface and a substance near the metal fine particles is detected using the induced localized plasmon resonance. When light is incident onto metal fine particles, such as gold or silver, a characteristic resonance spectrum is produced by the localized plasmon resonance. The absorbance at a resonance peak becomes larger as a dielectric constant of a medium near the metal fine particles becomes larger and shifts toward a long wavelength.

The specification of Japanese Patent No. 3452837 discloses a sensor constructed using a plurality of metal fine particles arranged on a substrate in isolation from each other. Here, the localized plasmon resonance sensor, which detects a refractive index of a medium near the fine particles by radiating light on a sensor unit and measuring an absorbance of light that permeates the sensor unit, is disclosed. Specifically, a system using a gold colloid about 20 nm in diameter is proposed. In addition, European Patent Application Publication No. 1445601A2 discloses a localized plasmon sensor, which has a layer-like substrate in which a plurality of micropores are formed, metal fine particles are filled in the micropores, and a metal thin film is arranged around the micropores on a surface of the substrate. It is described that this sensor can detect a minute refractive index change and binding with specified substances by using an interaction between localized plasmon resonance of fine particles and surface plasmon resonance of the nearby metal thin film.

On the other hand, as proposed by Felicia Tam et al. (J. Phys. Chem. B., 2004, Vol. 108, No. 45, p. 17290-17294), there is an example of a device structure that aims to enhance the detection capability by producing core shell type fine particles that are made by coating gold thin films on dielectric cores.

There is disclosed, in European Patent Application Publication No. 0965835A2, a system in which an interaction between a metal thin film and metal fine particles is used. Here, a sensor system combining a gold thin film formed on a substrate and gold-coated fine particles of a polymer formed on the gold thin film is proposed. This system is aimed at enhancing sensor characteristics by the interaction between surface plasmon resulting from the gold thin film of a foundation and localized plasmon resulting from the gold coating on surfaces of the fine particles of the polymer.

Since a measuring method using localized plasmon resonance does not need tagged molecules, such as fluorophores, the assay procedure is simple in comparison with a fluorescent immunoassay or a chemiluminescence immunoassay. In addition, since direct real-time monitoring of a process of an adsorption reaction on surfaces of metal fine particles is possible, applications in various kinds of assays are expected. Nevertheless, sufficient detection sensitivity was not obtained in affinity assays, such as an immunoassay, using those conventional target substance detecting devices that employ plasmon resonance.

DISCLOSURE OF THE INVENTION

The present invention provides a target substance detecting device, which is preferable to detect a trace amount of a target substance in a specimen by utilizing an interaction of localized plasmon resonance effectively, a target substance detecting method using it, and an apparatus and a kit therefor.

According to an aspect of the present invention, there is provided a target substance detecting device comprising a substrate, a structure disposed in isolation using metal on a surface of the substrate, and a target substance trapping substance disposed on the structure to detect a target substance using localized plasmon resonance, the structure being comprised of at least two metal layers and a non-conductive layer, the non-conductive layer being sandwiched by the metal layers.

The metal layers and the non-conductive layer preferably have the same shape two-dimensionally.

In the target substance detecting device, as a planar size of the metal layers, a distance between two points on an outer periphery of the metal layers is preferably in a range of from 10 nm to 1450 nm.

The metal layers and the non-conductive layer are preferably obtained by patterning layers that are constructed of these materials, respectively.

In the target substance detecting device, each of the metal layers preferably has a thickness of from 10 nm to 100 nm.

The non-conductive layer preferably has a thickness of from 10 nm to 100 nm.

In the target substance detecting device, the entire thickness of the layers that form the structure is in a range of from 30 nm to 300 nm.

The target substance detecting device preferably has a plurality of structures on the surface of the substrate. In the target substance detecting device, an interval between the plurality of structures is preferably in a range of from 50 nm to 2000 nm.

The metal layers are preferably constructed of any metal, which is selected from a group of gold, silver, copper, and aluminum, or an alloy thereof.

The non-conductive layer is preferably constructed of an inorganic oxide, polymeric material, or a mixture thereof.

The target substance trapping substance is preferably an antibody. The antibody is preferably an antibody fraction. The antibody fraction is preferably a multi-specific multivalent antibody.

According to another aspect of the present invention, there is provided a target substance detecting apparatus for detecting a target substance in a specimen using localized plasmon resonance, comprising:

the above holding means for holding a target substance detecting device; and a detecting means for detecting capture of the target substance by the device.

According to still another aspect of the present invention, there is provided a target substance detection kit for detecting a target substance in a specimen using localized plasmon resonance comprising:

the above target substance detecting device;

the above target substance detecting apparatus; and a reagent necessary for capturing the target substance on the device.

According to a further aspect of the present invention, there is provided a target substance detecting method for detecting a target substance in a specimen using localized plasmon resonance, comprising the steps of:

bringing the above target substance detecting device into contact with the specimen; and detecting the capture of the target substance on the device.

BRIEF DESCRIPTION OF THE DRAWINGS

FIG. 1A is a perspective view of a layered structure disposed on a substrate surface, and FIGS. 1B and 1C are sectional views in a plane vertical to the substrate;

BEST MODE FOR CARRYING OUT THE INVENTION

In the present invention, a region where localized plasmon is reinforced locally is generated by disposing a layered structure, which is constructed by sandwiching non-conductive layers with at least two metal layers in isolation on a substrate surface. It is possible to detect a trace amount of a target substance in a specimen, since susceptibility to a change in a dielectric constant near the structure increases when the localized plasmon is reinforced.

A target substance detecting device according to the present invention has a layered structure using metal layers formed on a surface of a substrate. Two or more layered structures can be disposed at intervals on the substrate. The shape of the layered structure, the layer thickness, and the structure interval affect a peak position of a resonance spectrum of the localized plasmon. Hence, the layered structure is required to have a shape, size, and disposition that provide a peak position that is suitable for measurement.

Figure 1A:
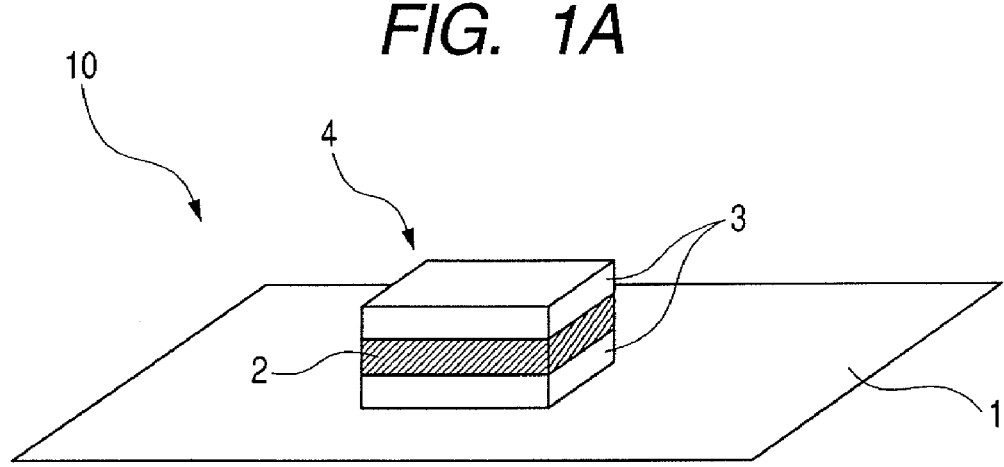
FIGS. 1A, 1B and 1C are schematic diagrams of a target substance detecting device according to the present invention.
Figure 1B:
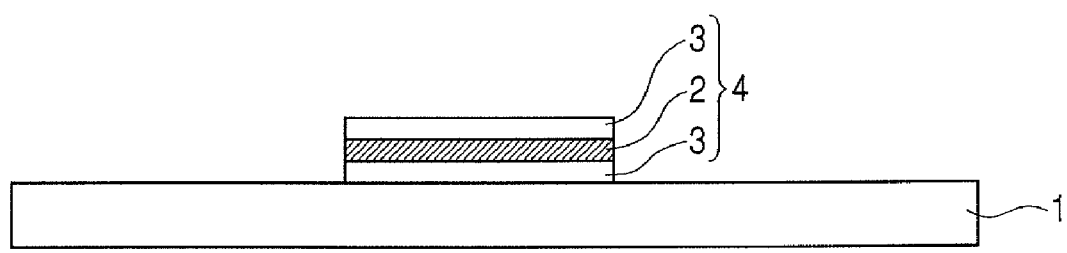
Figure 1C:
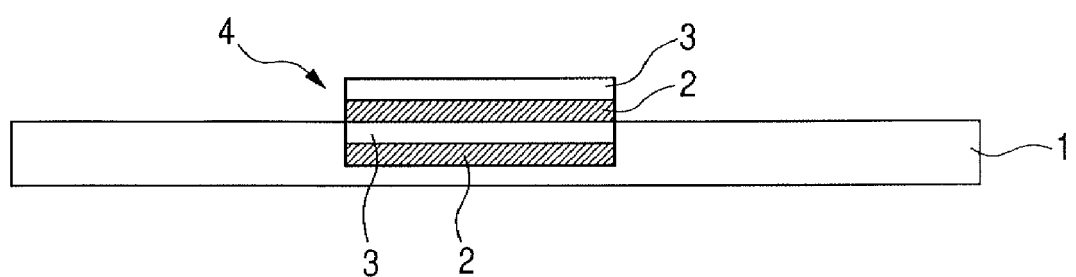

The layered structure is provided in isolation on a substrate surface, that is, as shown in FIG. 1A, such that a layered structure 4 does not contact another layered structure or an installed object on a substrate 1, or an end portion of the substrate, and that a tangent of a side face of the structure and a substrate surface is close. In addition, as shown in FIG. 1B, the layered structure may be formed so that it projects from the substrate surface, or as shown in FIG. 1C, it may have a portion buried in the substrate.

An embodiment of the present invention is explained in detail below with respect to every component.

Substrate

A substrate according to the present invention is a plate-like member, which functions as a supporting member on which a layered structure can be disposed in isolation. A material for the substrate is sufficient so long as it makes detection by a plasmon resonance method possible. Examples of such materials include glass, quartz, a resin, such as polycarbonate or polystyrene, ITO, and the like, which are optically transparent. The substrate may be covered for a reason other than supporting the structure, such as protection. When such covering is provided, the surface of the covering will be called the substrate surface as used in the present invention.

Layered Structure

The layered structure is stacked in a direction orthogonal to the substrate surface, and includes three or more layers constructed of a plurality of metal layers 3 and a non-conductive layer 2 sandwiched by them (see, for example, FIGS. 1A to 1C). It is preferable that the metal layers and non-conductive layer are stacked in turn.

It is preferable that the thickness of each metal layer is within a range of 10 to 100 nm. It is preferable that the thickness of the non-inductive layer is also within the range of 10 to 100 nm. It is preferable that the entire thickness of the layered structure is within a range of 30 to 300 nm.

As a material for the metal layers, it is possible to use gold, silver, copper, aluminum, and an alloy thereof. A material for each metal layer, in the case of using a plurality of metal layers, can be selected independently, i.e., from different metallic materials. As for the non-conductive layer, similarly, a plurality of non-conductive layers can be independently selected.

As a non-conductive material for the non-conductive layer, it is possible to use any one of silicon oxide, silicon nitride, titanium oxide, aluminum oxide, porous silica, and a polymeric material, such as polyimide, polymethylmethacrylate, polystyrene, polycarbonate, polyvinyl phenol, polydimethyl siloxane, acrylic and epoxy, or a mixture, which consists of two or more of the above.

It is preferable for the shape of the layered structure observed on a substrate surface, when the substrate surface is viewed from above (hereinafter, a "planar shape" of a layered structure), to be such that the rate of the effectual detection area is increased and localized plasmon is greatly reinforced. Since nearby localized plasmons interact and localized plasmons are further reinforced, a planar shape leading to localized plasmons being close to one another is preferable.

Such a planar shape has (1) a loop portion, (2) a branch connection, (3) a lengthy contour, (4) a corner, (5) a small distance between edges and the like. Specific examples of the shapes are shown in FIGS. 2A to 2K.

FIGS. 2D, 2E, 2F, 2G and 2J can be classified as shapes having a loop portion. Since contour length of a layered structure becomes a total of two, that is, an outer periphery and an inner periphery, due a hollow portion surrounded by the loop portion, contour length is increased by the inner periphery. As a result, it is possible to expect that a contour of the planar shape, that is, an edge portion, which is a region where localized plasmon is reinforced, is extended. Further, since edges of the inside and outside of a ring are close, localized plasmons interact and localized plasmons are even more reinforced. In addition, when there is a hollow portion, even in a layered structure that has an outline in the same size, it is possible to reduce the distance between the edges. Although a minimum distance between an edge in FIG. 2A, which is a square without a hollow portion, and another edge (distance between edges) is a distance between two opposite sides, the distance between the edges in FIG. 2D with a hollow portion becomes a maximum distance p between an outer peripheral edge and an inner peripheral edge. Incidentally, an outer peripheral shape and an inner peripheral shape are not analogues in FIGS. 2G and 2J, although an outer peripheral shape and an inner peripheral shape of a loop are analogues in FIGS. 2D, 2E and 2F.

Figure 2A:
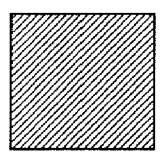
FIGS. 2A, 2B, 2C, 2D, 2E, 2F, 2G, 2H, 2I, 2J and 2K are schematic diagrams showing examples of planar shapes of the layered structure in embodiments of the present invention.
Figure 2B:
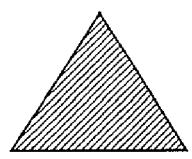
Figure 2C:
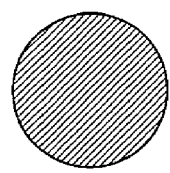
Figure 2D:
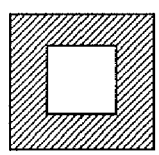
Figure 2E:
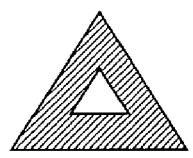

The presence of a hollow portion makes it possible to increase the number of corners. There is a total of eight corners in FIG. 2D, i.e., twice as many corners as in the structure shown in FIG. 2A, which does not have a hollow portion. It is also possible to provide a corner by a portion other than a loop portion. FIGS. 2D, 2E, 2F, and 2J show a ring shape, which consists only of a loop portion, and FIG. 2G shows a shape, which also has portions other than a loop portion.

It is also possible that one layered structure includes two or more loops.

Planar shapes shown in FIGS. 2D to 2K are constructed of belt-like portions. FIGS. 2D, 2E, 2G, 2H, 2I, 2J and 2K show shapes which are constructed of a plurality of belt-like portions. Among these, as for FIGS. 2G, 2H and 2K, a belt-like portion(s) penetrates another belt-like portion(s) mutually at a location(s) where the belt-like portions intersect (hereinafter, a "crossing(s)"). In FIGS. 2D, 2E, 2I and 2J, at least one of the belt-like portions is dead-ended in a crossing and does not penetrate to the other side. The belt-like portion(s) may be linear as in FIGS. 2D, 2E, 2G, 2H and 2I, or they may have a curvilinear portion as in FIGS. 2F, 2J and 2K. Although the shape of a crossing in FIGS. 2D, 2E, 2G, 2H and 2I is a polygon, such as a lozenge in FIG. 2E, a crossing in FIGS. 2J and 2K includes a circular arc. In addition, so long as a crossing is formed so that corners are round without being formed accurately in a polygon, even if a belt-like portion does not have a curvilinear portion, it can be said that it corresponds to a crossing having a circular arc. For example, it is a case where angles become round during the formation processes of FIGS. 2D and 2H for shapes of FIGS. 2J and 2K to be obtained.

Figure 13A:
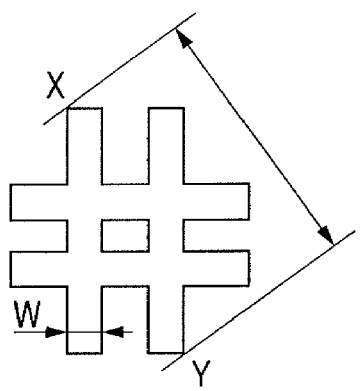
FIGS. 13A and 13B are drawings showing the standards for measuring the size of plane patterns of metal structures.
Figure 13B:
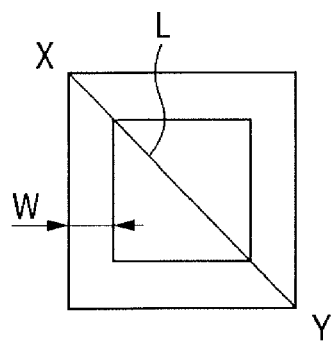

A width of a belt-like portion (hereinafter, a "belt width") is a difference between radii of an outer peripheral circle and an inner peripheral circle, for example, a circular ring pattern in FIG. 2F, or is a size shown by W in FIGS. 13A and 13B, respectively, where there is a parallel cross-like pattern and a rectangular ring pattern, which correspond to FIGS. 2G and 2D. Although the belt width is not particularly limited, so long as it is possible to form a layered structure and to obtain localized plasmon resonance, which is an object of the present invention, it is preferable that it be within a range of 10 to 100 nm. The belt width may be constant or may be changed in portions inside one layered structure.

When a maximum distance from one point on an outer periphery to another point on the outer periphery in a planar shape of a layered structure is 10 nm to 1450 nm, preferably within the range of 50 nm to 450 nm, it is possible to obtain localized plasmon resonance, which can more effectively achieve target substance detection sensitivity. In the circular ring pattern shown in FIG. 2F, a diameter of an outer peripheral circle is set within the above-mentioned range. Since the distance between points X and Y, which are shown in FIG. 13A, is at a maximum in the parallel cross-like pattern in FIG. 2G, this distance is set within the above-described range. Since the diagonal line L between points X and Y, which are shown in FIG. 13B, is at a maximum in the rectangular ring pattern in FIG. 2D, L is set within the above-described range.

The direction of the incident light is generally perpendicular to the substrate. However, making the light incident onto the metal structure at an oblique angle enables the light to undergo a shift in phase between the layers as a result of the interaction between the metal layer and the incident light. In the same manner, the phase of the plasmon resonance also shifts between the layers so that the effect by the interaction of the mode, i.e. phase shifting as well as the interaction by the neighboring location of the metal layers, can be utilized.

Disposition of Layered Structure on Substrate

Figure 3:
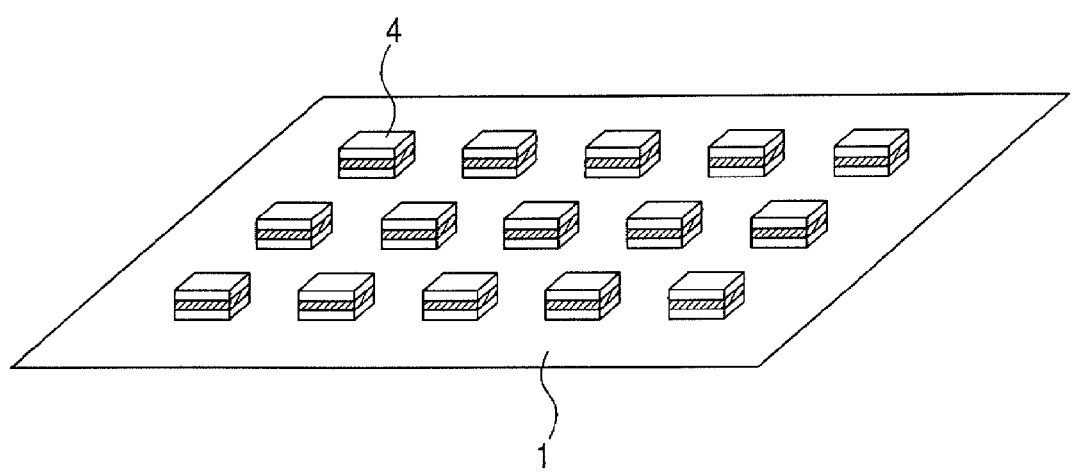
FIG. 3 is a schematic diagram showing an example of trapping bodies on the detecting device in the embodiment of the present invention.

At least one layered structure is provided on a substrate, as necessary. An interval between layered structures in the case of the plurality of ones is 50 nm to 2000 nm, or more preferably 150 nm to 1000 nm. This is because the interaction between the layered structures by the localized plasmon affects both the distribution and the strength of an electric field. As the interval becomes large, disposition density of the layered structures decreases so that the signal strength weakens, and hence, a special optical system to conduct the measurement becomes necessary. A planar shape and its size can be independently set for every layered structure. Nevertheless, in view of production efficiency of the layered structures and simplicity in the structure of a detection system and the like, as shown in FIG. 3, it is preferable to dispose the layered structures 4 with the same shape and size in an array on the substrate 1 that is several millimeters square. Such disposition makes it easy to measure transmitted, scattered, or reflected light.

Production Process

The process of producing metal layers is explained below using FIGS. 5A to 5F.

Figure 5A:
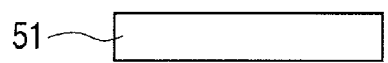
FIGS. 5A, 5B, 5C, 5D, 5E and 5F are diagrams for explaining a production method of the detecting device in an embodiment of the present invention.
Figure 5B:
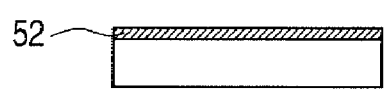
Figure 5D:
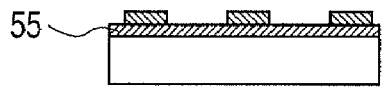
Figure 5E:
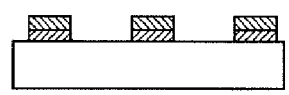
Figure 5F:
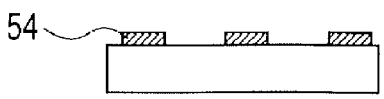

A substrate 51 is prepared (FIG. 5A). Here, in order to make the adhesion of the substrate and metal layer desirable, an adhesive metal thin film, such as chromium or titanium, may be disposed between the substrate and metal layer. Next, a metal thin film 52 is formed by a sputtering method or a vacuum deposition on the substrate 51 (FIG. 5B). An electron beam resist 53 is formed by spin coating thereon (FIG. 5C), an exposure is performed by an electron beam lithography system, and an after-development resist pattern is obtained (FIG. 5D). Then, the unnecessary metal thin film 55 is etched (FIG. 5E), and the resist is removed to form an array-like metal layer 54 (FIG. 5F).

For patterning, besides the electron beam lithography system, it is possible to use a focused ion beam processing device, an X-ray aligner, and an EUV aligner.

Although the process of providing a non-conductive layer also conforms to the process of providing the metal layer, a sputtering method, a CVD method, a vacuum deposition, a spin coating method, or the like is selected suitably as film formation means according to the material that is used.

In order to form the layered structure, it is preferable to make several layered structures at once using a pattern after performing a layer formation process of each layer in the order of lamination, or it is also preferable to perform the lamination by repeating the patterning of each layer to form an array.

Figure 6A:
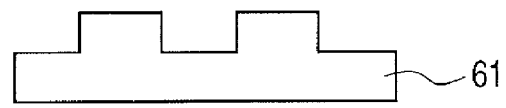
FIGS. 6A, 6B and 6C are diagrams for explaining a production method of the detecting device in an embodiment of the present invention.
Figure 6B:
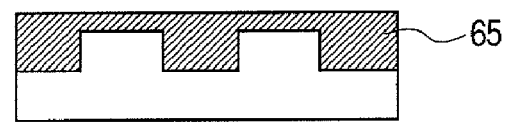
Figure 5C:
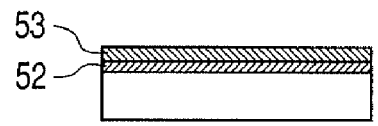
Figure 6C:
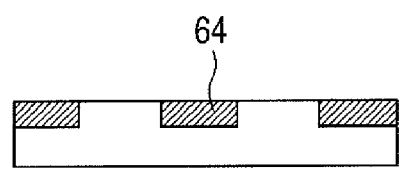

As shown in FIGS. 6A, to 6C, a production method using a fine convexoconcave substrate (FIG. 6A) produced by a mold method is also possible. A metal thin film is formed on a substrate 61 by the sputtering method or vacuum deposition. Then, a non-conductive material is formed suitably by the sputtering method, vacuum deposition, or spin coating method according to the material. Furthermore, film formation is repeated until a multilayer film 65 having a target substance structure is formed (FIG. 6B). Next, the metal thin film on the surface is ground to form a layered structure 64, which has the desired layered structure, on the substrate (FIG. 6C).

Figure 7A:
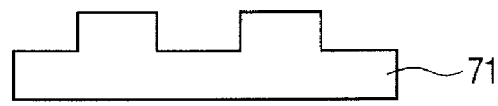
FIGS. 7A, 7B and 7C are schematic diagrams showing a part of a detecting apparatus in an embodiment of the present invention.
Figure 7B:
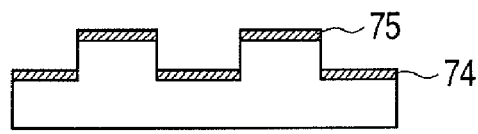
Figure 7C:
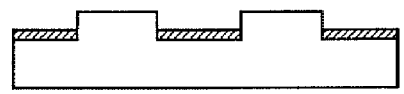

FIGS. 7A to 7C show a production method when the layered structure is thinner than a convexoconcave portion of the substrate. In this case, the convexity of the substrate 71 is higher than a surface of a layered structure 74. A thin film made of a metal or a non-conductive material may be formed on a wall surface of a convexoconcave portion. A thin film 75 on the convex and wall surface can be also removed using etchback by dry etching instead of grinding.

Surface with Capturing Capacity

Figure 4:
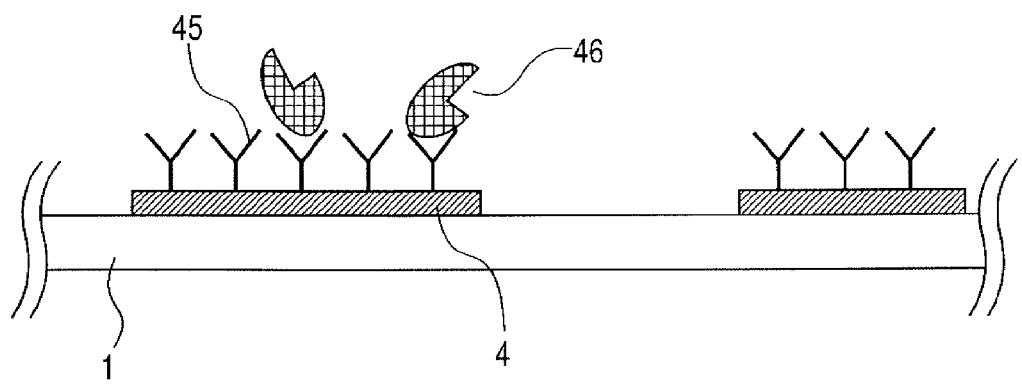
FIG. 4 is a diagram for explaining a production method of the detecting device in an embodiment of the present invention.

A target substance trapping substance is fixed on the layered structure formed as mentioned above to provide the device of the present invention with a capturing capacity. FIG. 4 shows the case where the antibody 45 is used as a target substance trapping substance. When a target substance 46 approaches the antibody 45 fixed to the layered structure 4, a specific complex is formed. Consequently, a dielectric constant, that is, a refractive index on a surface of a detecting device, changes.

Although a member of an arbitrary immunoglobulin class is preferably used as the antibody 45 trapping substance in the present invention, a derivative in an IgG class is more preferable. In addition, an antibody fraction fragmented by an arbitrary method may be sufficient as the antibody 45. An antibody fraction means an arbitrary molecule or a complex of an antibody that is shorter than the total length of the above-mentioned antibody or an immunoglobulin. Preferably, the antibody fraction provides a substantial part of the specific binding capability of a full-length antibody. Examples of the antibody fraction include a multispecific multivalent antibody, such as Fab, Fab', F(ab')$_2$, scFv, Fv, a diabody, and a triabody, and an Fd fragment. Since it becomes possible to perform the capture closer to the detecting device when using an antibody fraction, high detection sensitivity can be obtained. In addition, since a multi-specific multivalent antibody has specific recognition capacity to each of a detecting device and a target substance, it is possible to fix a trapping substance on a detecting device simply and efficiently.

A complex of an enzyme and a substrate, and a complementary base pair by hybridization of DNA, are also examples of the complex in the present invention. One of these complexes will be used as a trapping substance for the other. These trapping bodies are fixed on a surface of a detecting device by a physical or chemical method.

In order to prevent an unnecessary signal caused by adsorption of an impurity, it is also useful to coat the surface of the detecting device. Examples of a coating material include skim milk, casein, bovine serum albumin, a phospholipid, polyethylene glycol, and their derivatives.

Detecting Apparatus

Figure 8:
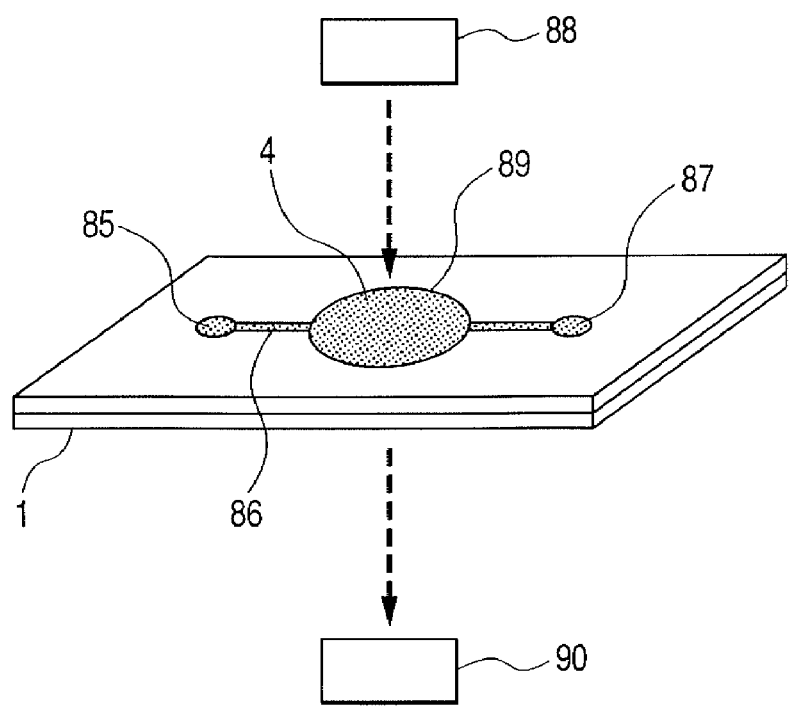
FIG. 8 is a block diagram of the detecting apparatus in an embodiment of the present invention.

A target substance detecting apparatus using a device with the above-mentioned structure is explained below. The detecting apparatus according to the present invention includes a holding means for holding the device with the above-mentioned structure and detection means for detecting a signal from the device. An example of the detecting apparatus according to the present invention is shown in FIG. 8.

The detection means is constructed of an optical detection system 90, which is constructed of a light source 88, a spectroscope, and lenses, and a solution sending system, which is constructed of an inlet 85 from which a specimen flows into the detecting apparatus, a reaction well 89 for moving the specimen to a detecting device and reacting it with the device, a pass 86, an outlet 87 from which the specimen flows out of the detecting apparatus, a solution sending mechanism, and the like. A light source that can cover a wavelength region from visible to near infrared is used. As the optical measurement, an absorption spectrum, a transmission spectrum, a scattered spectrum, and a reflection spectrum can be used. Most preferably, a peak wavelength of the absorption spectrum or absorption intensity at its peak is used. When the detecting device according to a layered structure specifically binds a target substance, localized plasmon resonance changes from an unbound state, the peak wavelength of the absorption spectrum shifts toward a long wavelength, and the absorption intensity simultaneously increases. It is possible to determine the amount of the target substance according to an extent of the shift from a calibration curve for the target substance, which was prepared beforehand. Since the detecting device of the present invention uses localized plasmon resonance, local electric field enhancement occurs near the layered structure. This phenomenon can also be applied to measuring methods, such as surface enhanced Raman spectroscopy (SERS) and surface plasmon fluorescence spectroscopy (SPFS), and the fixed quantity of the target substance by these methods is also possible.

It is easy to produce the reaction well and pass with a poly dimethyl siloxane (PDMS) substrate used in a so-called PTAS (Micro Total Analysis Systems) type device. This PDMS substrate will be bonded together with a substrate on which the detecting device is produced to be used in a shape as shown in FIGS. 7A to 7C. A micro piston pump, a syringe pump, or the like is used as the solution sending mechanism.

Figure 9:
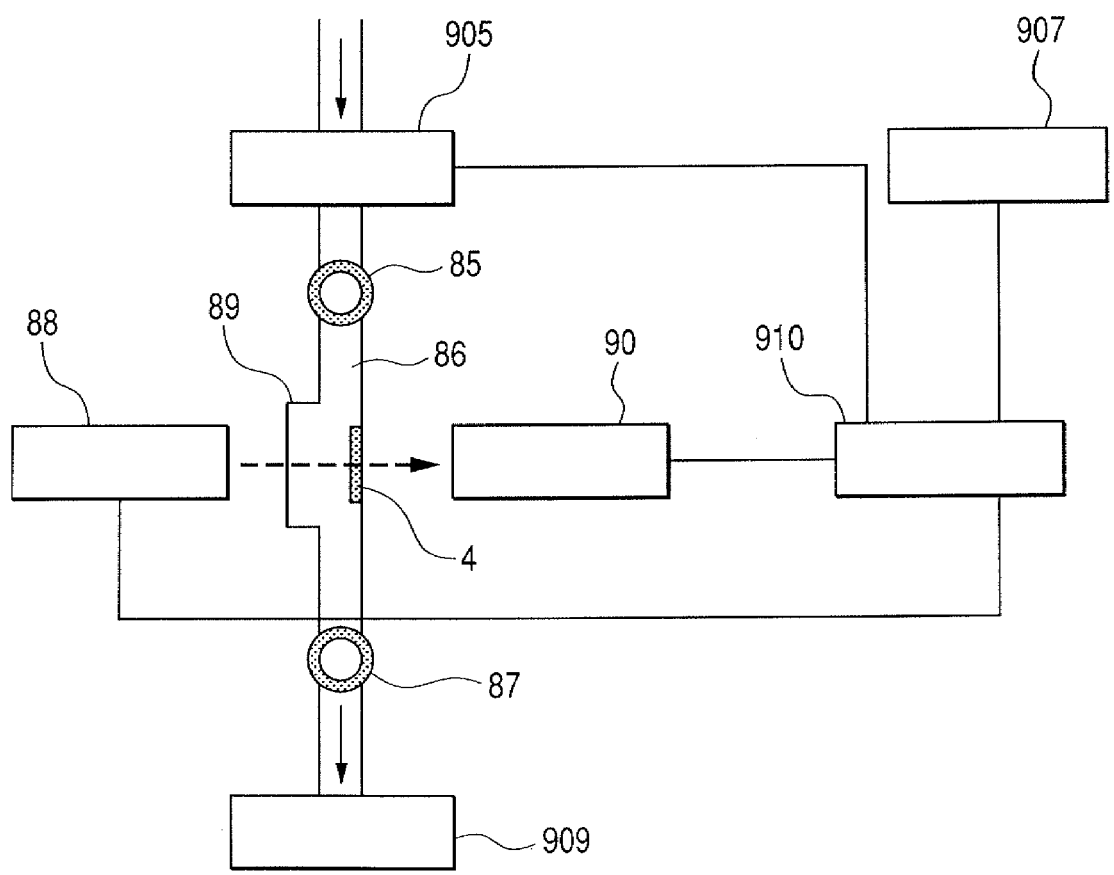
FIG. 9 is a schematic diagram of a detecting apparatus in the first example.

Next, a typical usage form is shown in FIG. 9. First, a specimen including a target substance is introduced into the reaction well 89, in which the detecting device 4 is disposed, through the pass 86 from the inlet 85 by the solution-sending pump 905. Incubation at a fixed amount of time is performed, and a transmission spectrum at that time is measured with a spectrophotometer 90. The transmission spectrum is compared in a central processing unit 910 with calibration data prepared beforehand, and measurement results, such as concentration and reaction rate, are displayed on a display unit 907. If necessary, a phosphate buffer and the like may be introduced from the inlet 85 as a cleaning fluid before the measurement, and the reaction well 89 may be washed. Here, it is possible to measure statically a spectral change after a fixed period of time. Also, it is possible to perform dynamically a real-time measurement of the change. In that case, it is possible to acquire a time rate of change and the like as new information.

Biological materials (protein, nucleic acid, sugar chain, lipid and the like), allergen, bacteria, virus and the like are preferable target substances to be captured. Furthermore, the detecting apparatus can be applied preferably to a so-called biosensor using an organism origin substance, or its allied substances as a trapping substance component regardless of medical use, industrial use, and home use. Thereby, it is possible to detect a trace amount of a target substance in a specimen.

Detection Kit

It is possible to construct a target substance detection kit using at least the apparatus with the above-mentioned structure, the detecting device with the above-mentioned structure, and a reagent required for capturing a target substance using the device.

EXAMPLES

The present invention is specifically explained below using Examples. In addition, the present invention is not limited only to the following Examples.

First Example

Figure 10:
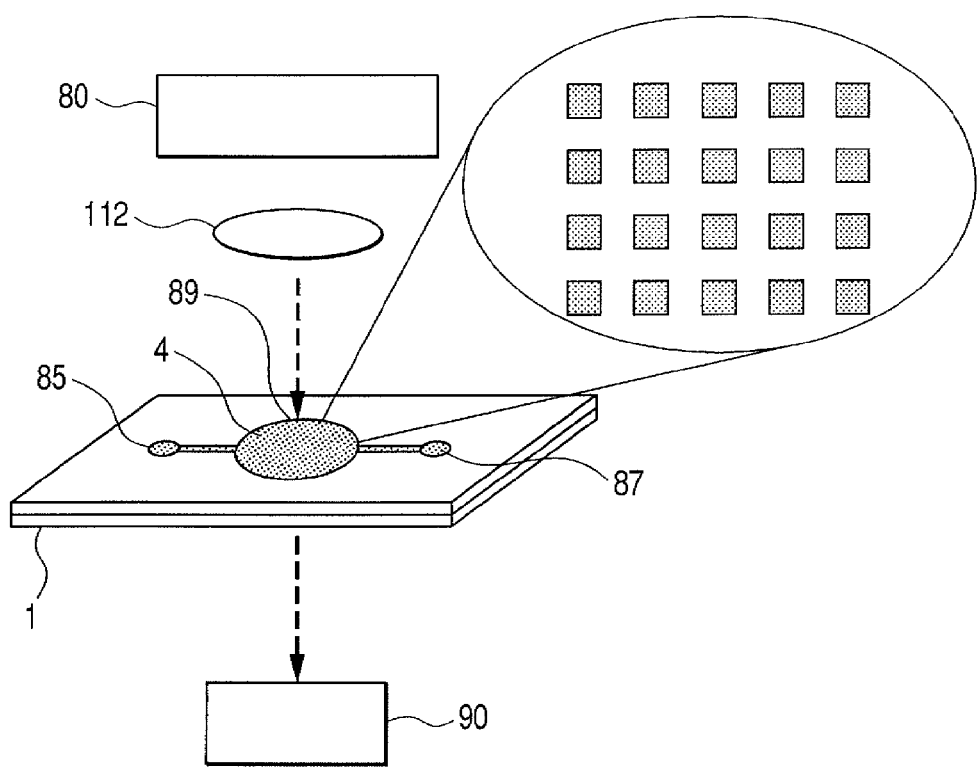
FIG. 10 is an example of a change of a detection spectrum (absorption spectrum) in the first example.

A schematic structure used in this example is shown in FIG. 10. Here, the detecting device 4 is produced by performing patterning of a gold structure with a film thickness of 20 nm on a quartz substrate with a film thickness of 625 µm using an electron beam lithography system. Film formation of each layer is performed one by one by a sputtering method. An external form of the layered structure is a 150 nm×150 nm square pattern. The layered structure, from the top, is made of three layers of a 20-nm gold thin film, a 10-nm silicon oxide film, and a 20-nm gold thin film. The interval between the structures is 400 nm, and the structures are disposed in a 3 mm×3 mm region in an array.

A method of fixing an anti-AFP (α-fetoprotein) antibody, which is a target substance trapping substance used in this example, to a surface of the gold structure so as to provide the structure surface with the capturing capacity will be shown. The above-mentioned structure surface is modified by dropping an ethanol solution of 11-Mercaptoundecanoic acid, which has a thiol group having high affinity for the gold, which is a material of the structure of this example, with a spotter or the like. Thereby, a carboxyl group is exposed on the structure surface. An N-hydroxysulfosuccinimide (made by DOJINDO LABORATORIES) aqueous solution, and a 1-ethyl-3-[3-dimethylamino]propyl]carbodiimide hydrochloride (made by DOJINDO LABORATORIES) aqueous solution are similarly dropped in a reaction region with a spotter. Thereby, a succinimide group is exposed on the structure surface. Furthermore, by binding streptavidin, the structure surface is modified with streptavidin. A biotinized anti-AFP antibody is fixed to this structure.

It is also possible to produce a plurality of pattern regions of the detecting devices 4 on the substrate 1 to fix immune bodies, which are different from each other, and to provide a structure (multisensor structure) that can be used to detect different target substances in a specimen on the same substrate. In this case, it is achieved by performing a fixing operations similar to the above-mentioned method using different immune bodies.

The AFP concentration in a specimen can be specifically measured as follows. A specimen that includes AFP, which is a target substance, is introduced from the inlet 85 in the produced device so that AFP can be captured by the structure. The specimen is discharged from the outlet 87. Then, a phosphate buffer is introduced from the inlet 85 for the reaction well 89 to be washed. Finally, a phosphate buffer is filled and an absorption spectrum of the gold structure is measured.

Figure 11:
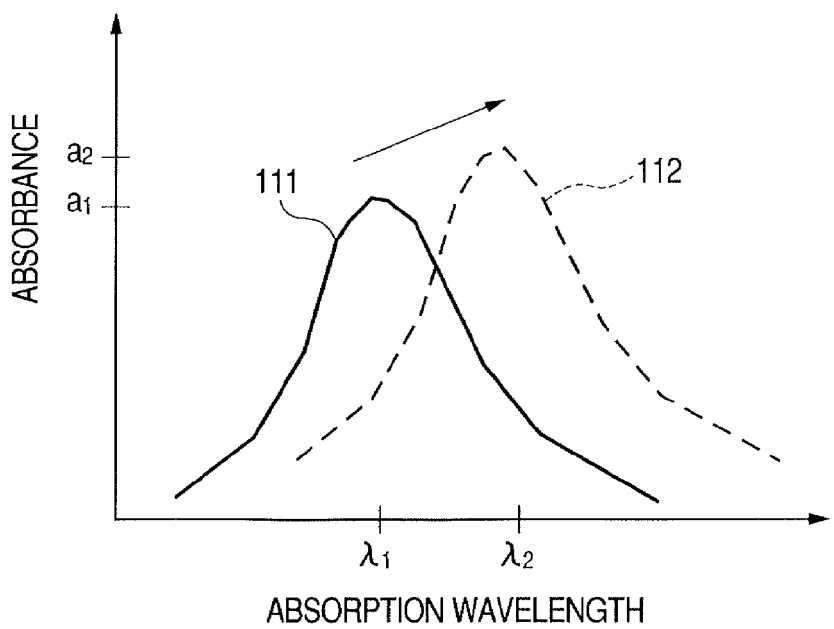
FIG. 11 is an example of a calibration curve of a specimen in the first example.
Figure 12:
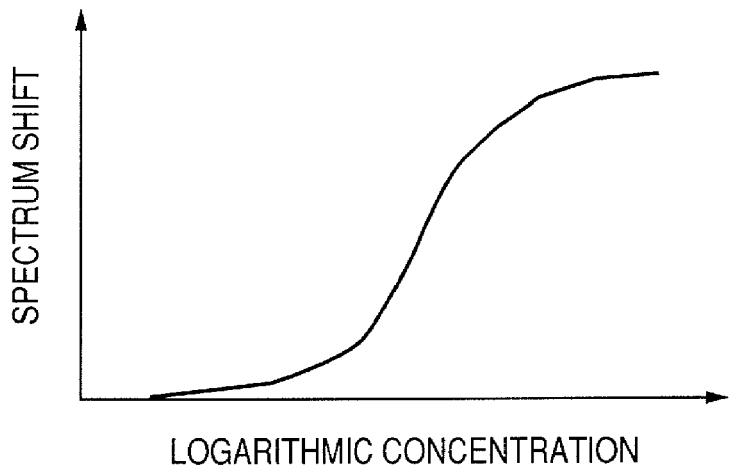
FIG. 12 is an example of the calibration curve.

When a curve 111 before a reaction is compared with a curve 112 after the reaction, as an example is shown in FIG. 11, the absorption spectrum shifts by a target substance bound to the surface of the detecting device because of a specific antigen-antibody reaction. Here, the correlation between a shift amount of peaks $a_1$ and $a_2$ of an absorbance of the absorption spectrum, or a shift amount of peaks $\lambda_1$ and $\lambda_2$ of an absorption wavelength, and the AFP concentration has been found with known AFP control solutions beforehand as a calibration curve in FIG. 12. Therefore, it is possible to find a trace of the AFP concentration of a specimen that has an unknown concentration.

Second Example

In this example, a fine convexoconcave substrate is produced by a mold method using a polycarbonate substrate. It is possible to produce the fine convexoconcave pattern in the same manner as a common optical disk. An external form of the structure is a 200 nm×200 nm square pattern. The layered structure, from the top, is made of a 20-nm gold thin film, a 40-nm acrylic resin, and a 20-nm gold thin film. The interval between the structures is 600 nm, and these structures are disposed in a 3 mm×3 mm region as an array. The gold thin films are formed by vacuum deposition and the acrylic resin thin film is formed by hardening by ultraviolet radiation after spin coating. Next, the unnecessary gold thin film 65 on the surface is ground to form the layered structure 64, which has the desired layer structure, on the substrate 61 (FIG. 6C).

In order to provide the surface of the structure with capturing capability, it is processed in a manner similar to that in the First Example. In this example, an anti-PSA (prostatic specific antigen) antibody, which is a target substance trapping substance, is fixed on the gold structure surface.

Similar to the First Example, when being compared before and after the reaction, the absorption spectrum shifts due to a target substance being bound to the surface of the detecting device because of a specific antigen-antibody reaction. The correlation between peak strength of the absorption spectrum, or a shift amount of a peak wavelength, and the PSA concentration has been found with known PSA control solutions beforehand. Therefore, it is possible to find a trace PSA concentration of the specimen that has an unknown concentration.

Third Example and First Comparative Example

Figure 2F:
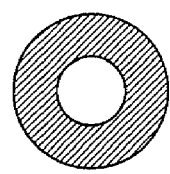
Figure 2G:
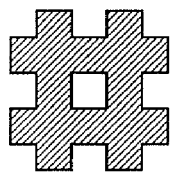

In this example, the metal structure is formed to have a ring-orbiting shape as shown in FIG. 2F, and has a layered structure. This structure is characterized by having not only a localized plasmon enhancement effect due to the ring shape, but also by having an enhancement effect due to the layered structure. The devices are produced by forming a gold thin film and a silicon oxide film by a sputtering method, patterning the structures using an electron beam lithography system, and an etching process, one by one, similar to the First Example. When being confirmed by a scanning electron microscope (SEM) image, an external form of a structure is 200 nm×200 nm, and line width is 50 nm. Depending on a degree of resolution of a rendering process, a shape of a crossing cannot be necessarily produced at rights. A 400-nm space is opened between structures and they are disposed in a 3 mm×3 mm region in the form of an array. In this example of stacking metals sandwiching a non-conductive material, in comparison with a case of not stacking metals and a non-conductive material (the First Comparative Example), that is, a case of only one layer of gold thin film pattern, the amount of the shift of the plasmon resonance peak wavelength to the refractive index change increases about 5 to 20%.

Fourth Example

Figure 2H:
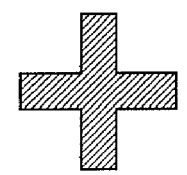
Figure 2I:
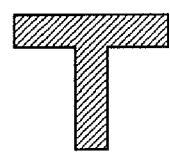
Figure 2J:
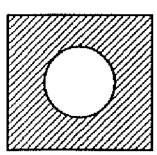
Figure 2K:
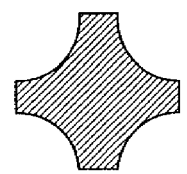

In this example, the shape of the layered structure is formed as shown in FIG. 2H. This structure is characterized by having not only a localized plasmon enhancement effect due to the crossing, but also by having an enhancement effect due to the layered structure. The devices are produced by forming a gold thin film and a silicon oxide film by a sputtering method, patterning structures using an electron beam lithography system, and an etching process, one by one, similar to the First Example.

Fifth Example

In this example, a bispecific antibody (diabody), which has specific affinity to two substances of gold, which is a material of a detecting device, and HEL (hen albumen lysozyme), which is a target substance, is used in the device described in the First Example in order to provide the surface of the metal structure with a capturing capacity. The bispecific antibody (diabody) used here is what is described in Japanese Patent Laid-Open No. 2005-312446. The regulated diabody is added in a detecting device portion with a phosphate buffer, and is washed with a buffer solution and used after incubation for about 30 minutes. According to the method of this example (using the diabody), as opposed to a chemical fixing method, it is possible to perform the fixing without negatively affecting affinity. Consequently, it is possible to reduce the amount of the trapping substance required for fixing on the detecting device.

Next, by the following operations, the HEL concentration in a specimen can be specifically measured.
(1) A specimen that includes HEL, which is a target substance, is introduced from an inlet 108 in the produced device for HEL to be caught on the structure.
(2) The specimen is discharged, and a phosphate buffer is introduced from the inlet 108 for an interior of a reaction well 107 to be washed.
(3) Finally, a phosphate buffer is filled and an absorption spectrum of the gold structure is measured.

When an absorption spectrum is compared before and after the reaction, the absorption spectrum is shifted by a target substance bound to a surface of the detecting device because of a specific antigen-antibody reaction. Here, the correlation between peak strength of the absorption spectrum, or a shift amount of a peak wavelength, and the HEL concentration has been found with known HEL control solutions beforehand. Hence, it is possible to find a trace of the HEL concentration of the specimen that has an unknown concentration.

Second Comparative Example

Figure 14:
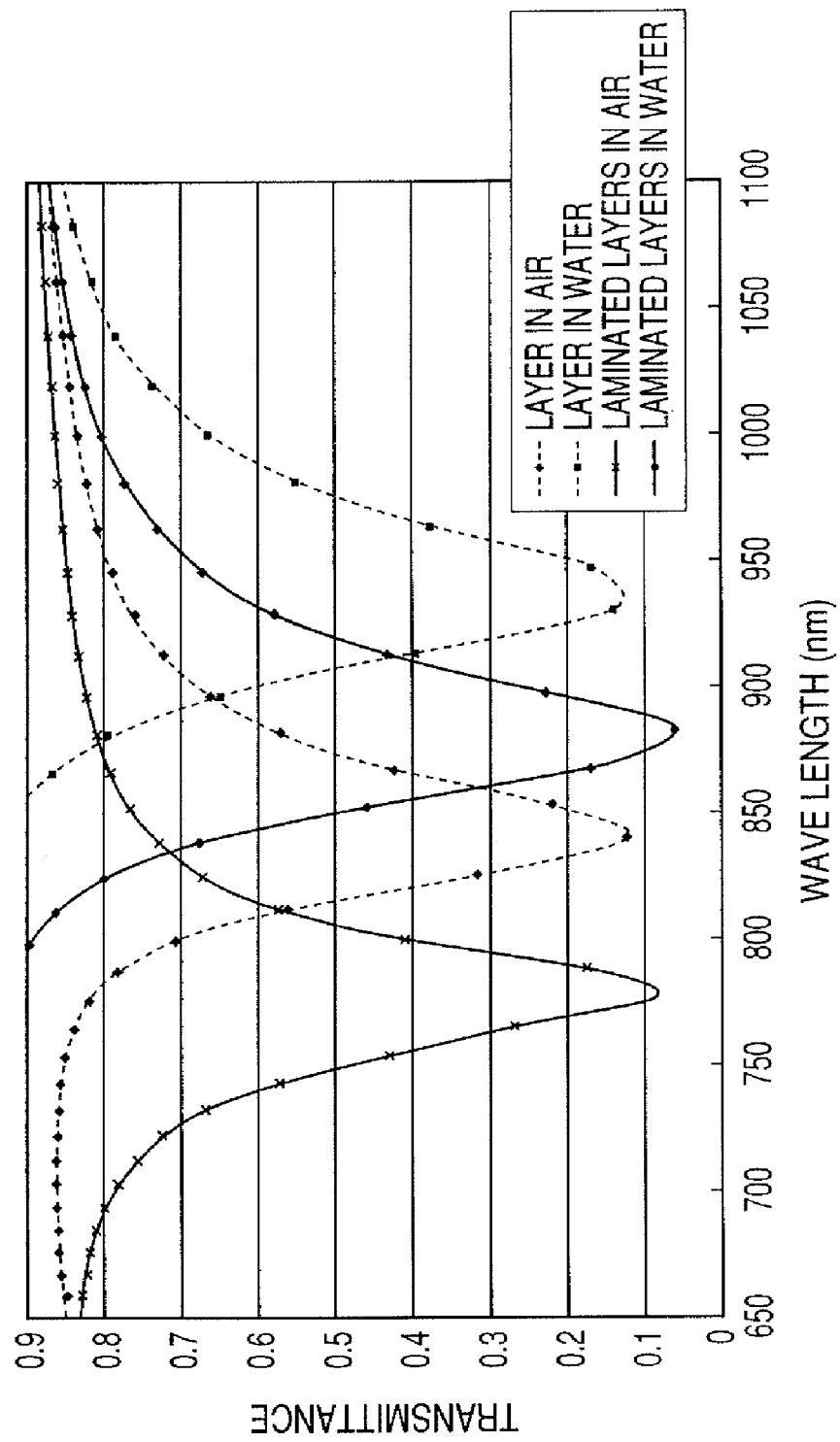
FIG. 14 are plots showing differences in detected absorption spectra in Comparative Example 2.
Figure 15A:
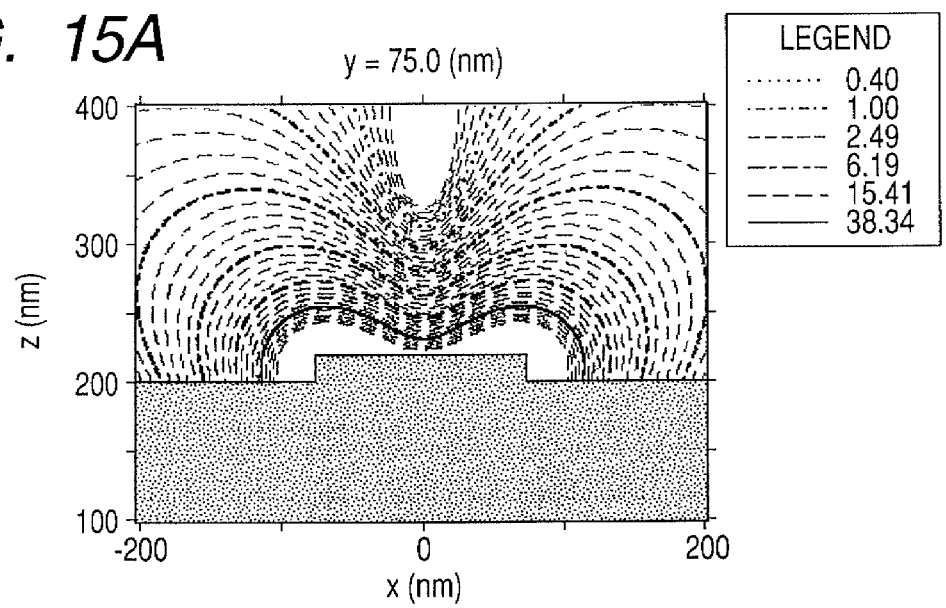
FIGS. 15A and 15B are drawings showing distributions of electromagnetic intensity of detecting devices in Comparative Example 2.
Figure 15B:
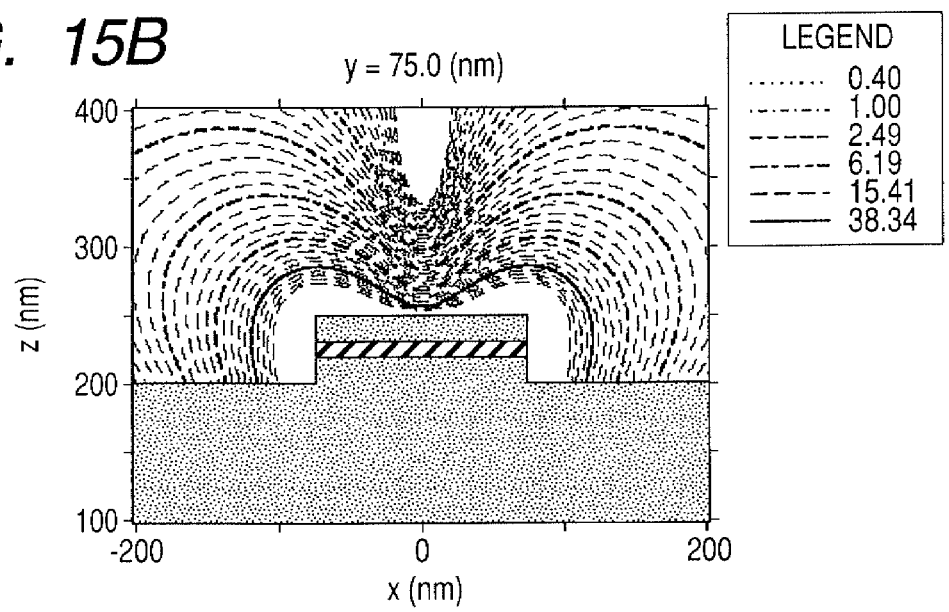

In this comparative example, the detecting device having a layered structure described in Example 1 is compared with another detecting device having a single layer structure, an external form of which is the same as the layered structure in Example 1: a 150 nm×150 nm square pattern and a 20 nm thick gold thin film. The results are obtained by analyzing the electromagnetic field with Finite Differential calculus of Time Domain (FDTD). FIG. 14 shows plasmon resonance spectra in water and in air as the results of the electromagnetic field analyses. In FIG. 14, the resulting spectra show the differences between the single layer structure and the layered structure (referred to as "Laminated layers structure" in the figure) in each medium in a transmittance to wavelength plot. According to FIG. 14, the shifts in the plasmon resonance peak due to the difference in refraction index at the layered structure and the single layer structure are estimated to be 325 nm/RIU and 270 nm/RIU, respectively. It is, therefore, understood that the use of the layered structure increases sensitivity by about 17%. FIGS. 15A and 15B show a simulated distribution of intensity of the electromagnetic field in the vicinity of the single layer structure and the layered structure, respectively. According to FIGS. 15A and 15B, it is observed that the intensive electromagnetic field in the vicinity of the layered structure is widely distributed in comparison with that of the single layer structure. Thus, the effect of the lamination of layers was observed in even distribution of intensity of the electromagnetic field, which is deemed to correlate to sensitivity.

This application claims priority from Japanese Patent Application No. 2005-223505, filed on Aug. 1, 2005, which is hereby incorporated herein by reference.

The invention claimed is:

1. A target substance detecting device using localized plasmon resonance comprising a substrate and a plurality of layered structures disposed on a surface of the substrate, each of the plurality of layered structures comprising at least two metal layers and a non-conductive layer, the non-conductive layer being sandwiched by the metal layers,
   wherein the metal layers are electrically separated from each other and give rise to localized plasmon resonance when receiving light which is emitted from a light source and which propagates in the air,
   wherein in a planar shape of the metal layers, a maximum distance from one point on an outer periphery to another point on the outer periphery ranges from 10 nm to 1450 nm,
   wherein the non-conductive layer has a thickness of from 10 nm to 100 nm, and
   wherein the plurality of layered structures are disposed isolated from each other on the substrate.

2. The target substance detecting device according to claim 1, wherein the metal layers and the non-conductive layer have the same shape two dimensionally.

3. The target substance detecting device according to claim 2, wherein the metal layers and the non-conductive layer have the same size two dimensionally.

4. The target substance detecting device according to claim 1, wherein the metal layers and the non-conductive layer are obtained by patterning layers which are constructed of these materials respectively.

5. The target substance detecting device according to claim 1, wherein each of the metal layers has a thickness of from 10 nm to 100 nm.

6. The target substance detecting device according to claim 1, wherein a thickness of whole layers which form the structure is in a range of from 30 nm to 300 nm.

7. The target substance detecting device according to claim 1, wherein an interval between the plurality of layered structures is in a range of from 50 nm to 2000 nm.

8. The device according to claim 1, wherein the metal layers are constructed of a metal, which is selected from a group of gold, silver, copper, and aluminum, or an alloy thereof.

9. The device according to claim 1, wherein the non-conductive layer is constructed of an inorganic oxide, polymeric material, or a mixture of them.

10. The target substance detecting device according to claim 1, wherein the target substance trapping substance is an antibody.

11. The target substance detecting device according to claim 10, wherein the antibody is an antibody fraction.

12. The target substance detecting device according to claim 11, wherein the antibody fraction is a multispecific multivalent antibody.

13. A target substance detecting apparatus for detecting a target substance in a specimen using localized plasmon resonance, comprising:

a holding means for holding a target substance detecting device according to claim 1; and a detecting means for detecting capture of the target substance by the device.

14. A target substance detection kit for detecting a target substance in a specimen using localized plasmon resonance comprising:

a target substance detecting device according to claim 1;

a target substance detecting apparatus for detecting a target substance in a specimen using localized plasmon resonance, comprising a holding means for holding the target substance detecting device and a detecting means for detecting capture of the target substance by the device; and a reagent necessary for capture of the target substance on the device.

15. A target substance detecting method for detecting a target substance in a specimen using localized plasmon resonance, comprising the steps of:

bringing the target substance detecting device according to claim 1 into contact with the specimen; and detecting capture of the target substance on the device.

16. The target substance detecting device according to claim 1, wherein the plurality of layered structures are disposed in an array on the substrate.

* * * * *